Figure 1:
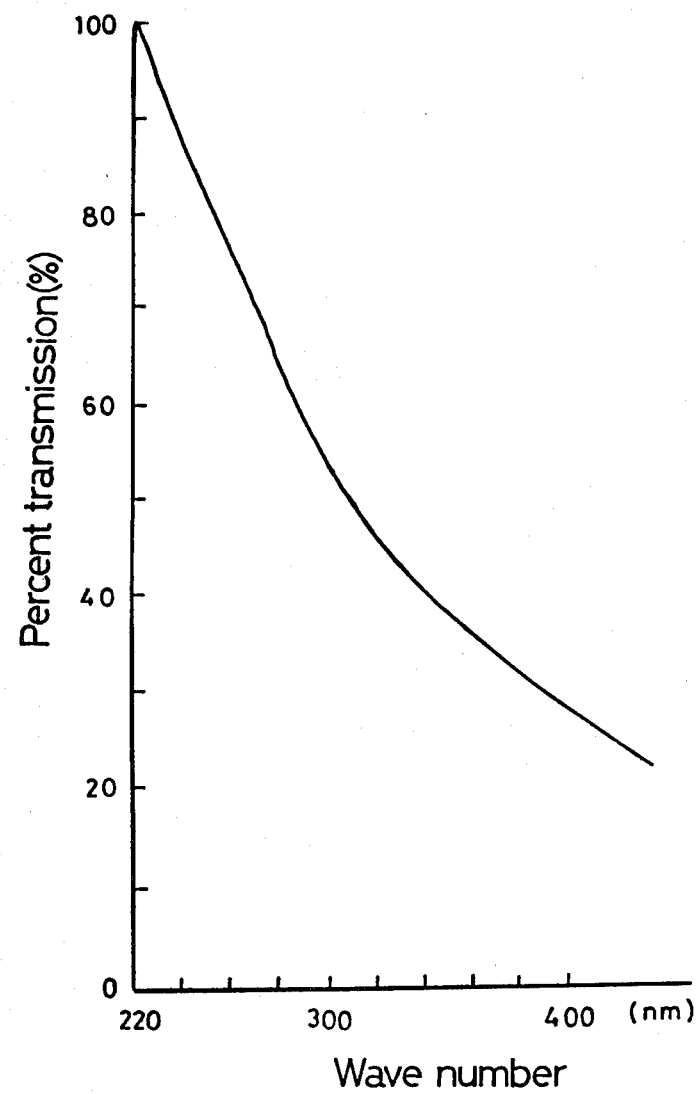

United States Patent [19]
Kojima et al.

[11] 4,442,087
[45] Apr. 10, 1984

[54] INTERFERON INDUCER, A PROCESS FOR PRODUCING THE SAME AND PHARMACEUTICAL COMPOSITION CONTAINING THE SAME

[75] Inventors: Yasuhiko Kojima, Yokohama; Seishi Konno; Sadao Tamamura, both of Tokyo; Takashi Hashimoto, Chofu; Nobuyuki Shibukawa, Tokyo, all of Japan

[73] Assignee: The Kitasato Institute, Tokyo, Japan

[21] Appl. No.: 282,468

[22] Filed: Jul. 13, 1981

[30] Foreign Application Priority Data

Dec. 10, 1979 [JP] Japan .................................. 54/160089

[51] Int. Cl.$^3$ ..................... A61K 31/69; A61K 39/00; A61K 45/02
[52] U.S. Cl. ........................................ 424/85; 424/195
[58] Field of Search ................................ 424/85, 195

*Primary Examiner*—Stanley J. Friedman
*Attorney, Agent, or Firm*—Wolder, Gross & Yavner

[57] ABSTRACT

An interferon inducer isolated from the plant tissue, having an elemental analysis of H:7.4±0.4%, C: 45.6±0.4%, N: 13.5±0.4%, P: 2.8±0.3% and a molecular weight of from about 100,000 to about 3,000,000 (mainly about 200,000 to about 1,000,000) and containing as main chemical constituents amino acids and phosporic acid. This substance is believed to be a homogeneous polymer of protein and phosphoric acid.

This substance has an excellent interferon inducing activity and low toxicity and is significantly active upon various viruses. This interferon inducer may be produced by extracting a substance having interferon inducing activity from the tissue of a plant of the genus Artemisia of the family Compositae or a variant thereof containing the said active substance with water and recovering the active substance from the extracted solution. The recovery may preferably be effected by ultrafiltration. Pharmaceutical composition of this invention comprises as active ingredient the said active substance in association with a pharmaceutical carrier or excipient.

15 Claims, 2 Drawing Figures

INTERFERON INDUCER, A PROCESS FOR PRODUCING THE SAME AND PHARMACEUTICAL COMPOSITION CONTAINING THE SAME

RELATED APPLICATION

This application is a continuation-in-part of Ser. No. 147,001 filed May 6, 1980 which is a continuation-in-part of Ser. No. 110,976 filed Jan. 10, 1980, both are abandoned.

BACKGROUND OF THE INVENTION

This invention relates to interferon inducer, a process for producing the same and pharmaceutical composition containing the same.

Interferon, hereinafter referred to as IF is a substance capable of acting upon animal or human cells to inhibit the growth of a virus and is a type of protein liberated from the cell in response to viral infection. The activity of IF is specific with respect to an animal species and non-specific with respect to a viral species and may vary, with differing conditions used for its induction. It is also known that the growth of certain animal type viruses may significantly be inhibited by IF under certain conditions.

A substance capable of acting upon animal or humans cells to induce IF is designated as an IF inducer. Thus, an IF inducer is of potential interest in the prevention and treatment of various human and animal diseases caused by viral infection. However, various known IF inducers have never been used in practice for such a purpose because of certain defects. Thus, for example, U.S. Pat. Nos. 3,583,893 (1971) discloses the production of a double-stranded ribonucleic acid as an IF inducer originating from a microorganism and describes in its prior art statement that many substances including bacteria, viruses, polysaccharides, mitogenic agents, endotoxin and the like stimulate interferon formation but none is of interest for routine use because of their inter alia toxicity, antigenicity and infectiousness. It has thus been believed that IF inducers isolated from microorganisms are in general disadvantageous for therapeutic use because of their high toxicity.

Examples of known mitogenic agents isolated from the tissues of higher plants include phytohemagglutinin (PHA) [Wheelock, Science, 149:301 (1965) and J. Biol. Chem. 212, 607–615 (1955)], pokeweed mitogen [Friedman et al, Proc. Soc. Exp. Med., 125:90 (1967) and J. Exp. Med., 124:859–972 (1966)] and concanavallin A [Willen et al., Cell. Immunol., 6:110 (1973) and Methods of Carbohydrate Chem., vol. VI, 108–110 (1972)] respectively isolated from the tissues of kidney bean, pokeweed and horse bean by extracting with a saline or buffer solution, treating the extracted solution with an alcohol, followed by purification with column chromatography. Due to their extremely low IF-inducing activity, however, no successful attempt has been made to use these mitogenic agents for preventing and treating various diseases cause by viral infection.

Other IF inducers isolated from higher plants are also known. That is, Kojima et al [Japanese Patent Application as laid open to public inspection as Kokai Koho 32107/78] disclosed an IF inducer which is believed to be a kind of heteropolymeric saccharide containing as main constituents hexose (48%), protein (5%) and uronic acid (40%), and having a molecular weight of more than 100,000. This substance is isolated from the root of *Angelica acutiloba* Kitagawa (known in Japan as Toki) by extracting the root with hot water to give an extracted solution, subjecting the same to dialysis to give a residue, adding acetone to the residue to give a precipitate and freeze-drying the same. The extracted solution may, if desired, be made up to a suitable quantity by concentrating under reduced pressure or by using a Diaflo membrane (MW 10,000), followed by dialysis. Subsequently, Kojima and Tamamura [Japanese Patent Application laid open to public inspection as Kokai Koho 99313/78] disclosed an IF inducer having a molecular weight of more than 20,000 (mainly more than 60,000) and containing as main constituents a 1-3 bonded glucose (hexose: more than 90%). This IF inducer is produced by extracting the peeling of a mulberry e.g. *Morus alba* L or *M. bombycis* Koidzumi with hot water, adding an organic solvent to the extracted solution to give a precipitate, adding a small amount of water to the same, subjecting the mixture to dialysis to give a residue and freeze-drying the same. If desired, the solution after extraction or before dialysis may be made up to a suitable quantity either by concentrating under reduced pressure or by using a Diaflo membrane.

These two IF inducers isolated from the tissues of higher plants have high IF-inducing activity and low toxicity and may be obtained readily and cheaply. However, the cheap and abundant supply of the raw material may cease as a result of the continuous use of these plants over many years as the source of Sino-Japanese traditional drugs.

SUMMARY OF THE INVENTION

This invention is based upon the discovery that a substance which we have isolated from the tissue of various plants of the genus Artemisia of the family Compositate (known in Japan as the genus Yomogi of the family Kiku) and variants thereof shows high IF-inducing activity and extremely low toxicity. Moreover, the isolation of the active substance may be effected readily and simply.

According to this invention, there is provided a substance having IF-inducing activity which is stable in the substantially pure form of an amorphous whitish powder and which possesses the following physico-chemical characteristics:

(1) Elemental analysis: H: $7.4\pm0.4\%$, C: $45.6\pm0.4\%$, N: $13.5\pm0.4\%$, P: $2.8\pm0.3\%$.

(2) Molecular weight: About 1,000,000 to about 3,00,000 (mainly about 200,000 to about 1,000,000).

(3) Melting or decomposing point: Melting point indefinite. Carbonized at about 220° C.

(4) Ultraviolet absorption spectrum: As shown in FIG. 1 (determined in 0.1 N NaOH) which is substantially unchanged in 1 N NaOH or water.

Figure 2:
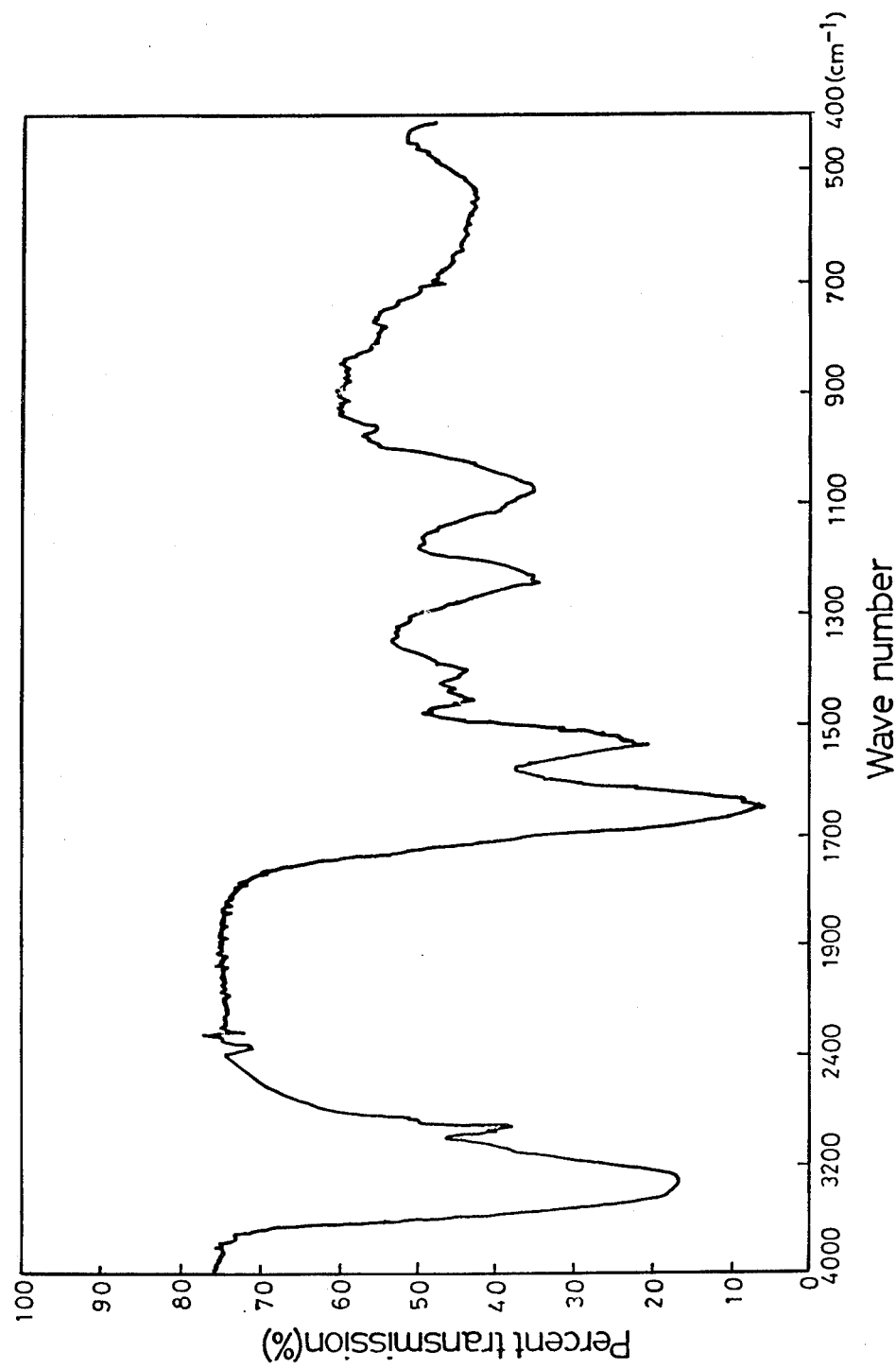

(5) Infrared absorption spectrum: As shown in FIG. 2 (KBr method).

(6) Solubility in various solvents: Soluble in water, readily soluble in aqueous solutions of sodium hydroxide, potassium hydroxide and ammonium hydroxide, and substantially insoluble in methanol, ethanol, propanol, acetone, chloroform and diethyl ether.

(7) Color reaction: Positive in ninhydrin reaction and Dittmer reaction. Negative in Folin's reagent and Elson-Morgan reaction.

(8) Nature: Acidic.

(9) Main chemical constituents:

(a) Amino acids (±0.6%) Aspartic acid ... 9.5%, threonine ... 4.9%, serine ... 4.7%, glutamic acid ... 8.4%, proline ... 3.1%, glycine ... 10.2%, alanine ... 11.2%, valine ... 6.9%, isoleucine ... 4.6%, leucine ... 7.8%, tyrosine ... trance, phenylalanine ... 2.9%, ammonia ... 12.1%, lysine ... 6.2%, histidine ... 1.8%, arginine ... 5.3%

(b) Sugar was not found.

(10) Optical rotation: $[\alpha]_D^{26} = +73°$ to $+79°$ ($+76$ in average) (c=0.47% in 0.1 N NaOH).

The elemental analysis of the active substance of this invention was determined by using a Perkin-Elmer Model 240 Elemental Analyzer (commercial product of Perkin-Elmer Corpn., U.S.A.). The molecular weight of the active substance of this invention was determined by analytical ultracentrifugation using a Spinco Model E Analytical Centrifuge (commercial product of Beckmann Instrument Inc., U.S.A.), ultrafiltration using an Amicon Ultrafilter with XM50, XM100A and XM300 membranes (commercial products of Amicon Corpn., U.S.A.) and UK10, UK50 and UK200 membranes (commercial products of Toyo Roshi K.K., Tokyo) and gel filtration using Sephadex G-200 (commercial product of Pharmacia Fine Chemicals AB., Sweden). The ultracentrifugation was effected under the following conditions and one broad peak having gentle slopes on both sides was observed: A sample (0.5–1.0%) of the active substance was suspended in a neutral solution of 0.1 M sodium chloride and centrifuged at 20° C. at a maximum run of 30,000 or 60,000 r.p.m. Supplementarily, column chromatography using gel filtration agents such as e.g. the series of Sepharose, Sephacryl (commericial products of Pharmacia Fine Chemicals AB., Sweden) and Bio-Gel (commercial products of Bio-Rad Laboratories Ltd., U.S.A.) was also used. All the results obtained were compared with the control values obtained, for example, by using standard references having identified molecular weights such as e.g. blue dextran 2000 (*2×10$^6$), $\alpha_2$-macroglobulin from horse serum (*8×10$^5$), thyroglobulin from bovine thyroid (*6.69×10$^5$), catalase from bovine liver (*2.1×10$^5$), aldolase from rabbit muscle (*1.58×10$^5$) and albumin from bovine serum (*6.7×10$^4$) (* ... standard molecular weight) Throughout various fractions having different molecular weights, substantially the same elemental analysis and IF-inducing activity (determined by the method of hereinafter described Experiment (1) were found. From these results, in combination with a broad single band observed by the electrophoresis (cf. hereinafter described Experiment (2) and a high recovery ratio (cf. hereinafter described Experiment (4), it is found that the active substance of this invention is not a mixture but a high molecular weight polymer composed of polymers having substantially the same chemical and biological characteristics, of which major portion is present in a range of from about 200,000 to about 1,000,000 and the minor portion is present in a range of from about 100,000–about 200,000 and about 1,000,000–about 3,000,000.

The UV and IR absorption spectra were determined respectively by using Hitachi 340 Recording Spectrophotometer (commercial product of Hitachi Limited, Japan) and Shimazu Recording Infrared Spectrophotometer IR-27G (commercial product of Shimazu Seisaku-sho, Japan).

The amino acids present were determined by hydrolysis with 6 N HCl at 110° C. for 48 hours in vacuo, followed by analysis using a Technicon Amino Acid Autoanalyzer Type NC-1 (commercial product of Technicon Corpn., U.S.A.) and the sugars present were determined by hydrolysis with 0.1 N sulfuric acid at 80° C. for 20 minutes and with 1 N sulfuric acid at 100° C. for 2 hours respectively, followed by analysis using a Technicon Sugar Autoanalyzer Type N-1 (commercial product of Technicon Corpn., U.S.A.).

The active substance of this invention also preferably and readily soluble in alkaline solutions and substantially insoluble in organic solvents.

The following tests were effected to ascertain that the active substance of this invention repesents an IF inducer.

(1) IF-inducing activity:

Samples of the active substance of this invention were used to induce IF in the cells and serum of test animals and the activity of the resultant IF was determined by the methods hereinafter described in Experiment 1. The results shown in Table 1 indicates that the IF inducing activity is positive.

TABLE 1

| Activity in vitro | Concentration of sample (μg/ml) | | | |
|---|---|---|---|---|
| | 10 | 1.0 | 0.1 | 0.01 |
| | 100 | 100 | 93 | 10 |

TABLE 2

| Activity in vivo | Time of collection of blood after administration (hour) | | | | |
|---|---|---|---|---|---|
| | 0 | 1 | 2 | 4 | 6 |
| Rabbit 1 | 10 | 55 | 480 | 95 | 44 |
| Rabbit 2 | 10 | 25 | 230 | 50 | 23 |

*Dose = 500 μg/ml

Table 2 indicates that the results obtained by the method hereinafter described in Experiment 1 using two rabbits show the activity reaches its maximum 2 hours after administration. It was also confirmed that by the method of Experiment 1, IF was induced in the body of the test animals by the action of the IF inducer of this invention.

(2) Stability of the IF inducer: Samples (each 1 mg) of the IF inducer of this invention were respectively dissolved in water (each 1 ml) and heated at 100° C. for a given time or at a given temperature for one hour, and was then treated by the method of hereinafter described in Experiment 1 (in vitro method) to obtain the results shown in Tables 3 and 4 indicating a high heat stability of the IF inducer of this invention.

TABLE 3

| Heating temperature (°C.) [Heating time: one hour] | IF activity at concentration of sample (μg/ml) | | | |
|---|---|---|---|---|
| | 10 | 1.0 | 0.1 | 0.01 |
| Untreated | >100 | >100 | 70 | <10 |
| 37 | >100 | >100 | 75 | <10 |
| 60 | >100 | >100 | 73 | <10 |
| 80 | >100 | >100 | 70 | <10 |
| 100 | >100 | >100 | 75 | <10 |

TABLE 4

| Heating time (hour) | IF activity at concentration of sample (μg/ml) | | | |
|---|---|---|---|---|
| | 10 | 1.0 | 0.1 | 0.01 |
| Untreated | >100 | >100 | 70 | <10 |
| 1 | >100 | >100 | 75 | <10 |
| 4 | >100 | >100 | 73 | <10 |
| 8 | >100 | >100 | 65 | <10 |

TABLE 4-continued

| Heating time (hour) | IF activity at concentration of sample (μg/ml) | | | |
|---|---|---|---|---|
| | 10 | 1.0 | 0.1 | 0.01 |
| 24 | >100 | >100 | 30 | <10 |

Heating temperature: 100° C.

From the above-mentioned characteristics, it has been found that the active substance of this invention conforms to widely recognized definition of any IF-inducer because it induces IF in animal cell or serum in vitro or in vivo, which is inactivated with 0.08% trypsin at 37° C. for 2 hours, and moreover, its activity is specific with respect to an animal species and nonspecific with respect to a viral species.

It is thus believed that the active substance of this invention is not only a new IF inducer but also a new substance because no such a substance has, to our knowledge, ever been reported in the art. For example, mitogenic agents such as phytohemagglutinin, pokeweed mitogen and concanavallin A described in the literatures are types of protein having very weak IF-inducing activity which is inactivated on heating at 56° C. for 5 hours, on the contrary to high heat stability and high IF-inducing activity of the active substance of this invention. The known IF inducers isolated from the root of *Angelica actiloba* Kitagawa is high molecular and its IF-inducing activity is not inactivated on heating at 100° C. for one hour. However, its chemical constituents and infrared absorption spectrum are different from those of the active substance of this invention. The known IF inducer isolated from the peeling of mulberry root contains as main constituent a 1-3 bonded glucose and has a different molecular weight. Moreover, the mitogenic activity which is found in the known IF inducers originating from bactrial endotoxin and higher plants such as *Angellica actiloba* and mulberry is very low in the IF inducer of this invention.

Various plants of the genus Artemisia which may be used as a source of the product of the IF inducer of this invention contain, for example, absinthin, anabsinthin, artemisin, paraffin, cinemole, semicarbazone, 1-camphor, sesquiterpene, cardiene, caryphyllene, sesquiterpene alcohol, artemisia ketone, α-pinene, camphene, bornol, cuminaldehyde, phenol, acetic acid, butyric acid, hexanol, benzylalcohol, methylbutyric acid, hexanol, benzylalcohol, methylbutyrate, cuminal, caryphyllene oxide, pentascosane, artemisiaalcohol, β0pinene, capillen, capillon, santonin, α-thujon, monogynin, mibulacton, cerylalcohol, carnaubic acid, hentriacontane, ricosanol, vitamins A, B, C, D and other low molecular substances, all of which are different from the IF inducer of this invention with respect to the physicochemical and biological characteristics and have no IF inducing activity.

It was no previously known, to our knowledge, that any plant of the genus Artemisia contains a substance having IF-inducing activity, as reported, for example, by Keisetsu Otsuka [Kanpo, Geschichte, Theorie und Praxis der Chinesisch-Japanischen traditionelen Medizin, 165-189 (1976)], Richard Hyatt [Chinese Herbal Medicine, 113 & 141 (1978)] and John D. Keys [Chinese Herbs, Their Botany, Chemistry & Pharmacodynamics, 216-220 (1978)].

According to another feature of this invention, there is provided a process for producing an IF inducer from the plant tissue, comprising extracting the said IF inducer with water from the tissue of a plant of the genus Artemisia or a variant thereof containing the said IF inducer at a temperature from ambient to the boiling point of the extraction mixture for a period sufficient to extract a major portion of the said IF inducer present in the tissue, forming a supernatant from the extracted solution, fractionating the supernatant to yield fractions containing a major portion of the IF inducer present in the supernatant, and recovering the IF inducer therefrom.

The plants which may be used for the process of this invention are both grown abundantly in the wild and are cultured in various countries of the world, and are liable to form various variants such as mutants and hybrids naturally or artificially. It is believed that there are about 30, 120 and 60 species in Japan and China, North America and Europe respectively, and some of these plants have been used over many years, for example, as foodstuffs, folk cures or as raw material for the prepration of medicaments. However, to our knowledge, it has never been reported in the art that a substance having IF inducing activity is present in the tissues of these plants. If desired, the plant of the genus Artemisia may, it is believed, be obtained from the Germplasm reservoir maintained by the US Department of Agriculture at the Plant Introduction Station, Washington State University, Pullman, Washington, U.S.A.

Any and all plants of the genus Artemisia containing the IF inducer may be used as a source of the process of this invention. The following plants are merely indicated by way of example:

*Artemisia princeps* Pamp; *A. absinthium* L.; *A. maritima* L.; *A. kurramensis* Qaz.; *A. montana* Pamp.; *A. feddei* Lev. et Van.; *A. japonica* Thun.; *A. keisumeana* Miq.; *A. stolonifera* Komar.; *A. monophylla* Kitam.; *A. stelleriana* Bess.; *A. capillaris* Thun.; *A. vallesiaca* All.; *A. dracunculus* L.; *A. ludoviciana* Nutt.; *A. arbuscula* Nutt.; *A. tridentata* Nutt.; *A. filifolia* Torr.; *A. caudata* Michx.; *A. lindleyana* Bess.; *A. frigida* Willd.; *A. biennis* Willd.; *A. campestris* L.; *A. molinieri* Quez and variants thereof.

The botanical names referred to in this specification are designated with reference to "Yakuyo Shokubutsu Dai Jiten" edited by Kariyone and Kimura and published by Hirokawa Shoten, Tokyo (1974); "Saishin Yakuyo Shokubutsu" by Kariyone and Kimura and published by Hirokawa Shoten, Tokyo (1978); "Flora of Japan" by Ohwl and published by Shibundo, Tokyo (1965); "North American Flora" vo. 34, edited by P. A. Rydberg and published by The New York Botanical Garden (1916); "Illustrated Flora of the Pacific States", vol. IV by Stanford University Press, CA (1965)' "Flora Europaea", vol. 4 edited by T. G. Tutin et al and published by Cambridge University Press, London (1976) and "The Flora of Canada" by H. J. Scoggan and published by National Museum of Canada, Ottawa (1979).

Although all tissues of the plant may be used for the process of this invention, additional operation may be needed to remove soil from the root of the plant. Both the leaf and stem contain substantially the same amount of the active substance of this invention and the amounts of the IF inducer contained in various tissues of a plant are substantially unchanged before and after the flowering period. For better preservation and exraction, it is preferred to use the dried plant, although it is possible to use the fresh material. The drying method is optional (e.g. natural drying, drying in hot air etc.). If desired, the material may be washed with water before use.

The extraction may be effected with water at any convenient temperature e.g. from ambient to the boiling point of the extraction mixture. As the IF inducer of this invention is particularly soluble in water under alkaline conditions (e.g. at a pH of 7 to 10), it is preferred to adjust the pH of water before use, for example, with a suitable buffer solution, sodium hydroxide, potassium hydroxide or ammonium hydroxide. The extraction may be effected over any convenient period of time, usually 1–5 days at room temperature, which time may be shortened if the temperature of extraction is raised. Thus, extraction may be effected, for example, for a period of 30 minutes to 6 hours at 45°–80° C. with stirring. According to this invention, it is possible to exract a major portion of the active substance contained in the starting material (in some cases, more than 90%). However, the use of an excessively high temperature should be avoided because the quantity of the undesired impurities such as pigments, low molecular weight substances etc. appearing in the extract may thereby increases. It is also possible, if desired, to add a suitable antiseptic agent to the extracting water. The extraction may be effected continuously at intermittently and any convenient ratio of the extracting water to the raw material may be used.

It is also possible, if desired, to extract the active substance with a hydrophilic organic solvent incapable of dissolving the IF inducer of this invention such as e.g. methanol, ethanol, propanol, butanol, acetone and the like in any convenient amount e.g. 20–80%. In such a case, the extraction time and temperature may be convenient e.g. for 4 hours to 2 days at 40° to 80° C. The extraction may be effected in such cases by using a hydrophilic organic solvent in spite of the insolubility of the pure product of this invention in such solvents. Extraction using hydrophilic organic solvents may be effected, for example, when the extracted solution contains a mixture or complex of substances such as fatty acids, steroids, proteins, mono- or polysaccharides and the like. Whilst we do not wish to be bound by theoretical considerations, it is believed that extraction using such organic solvents is made possible by buffer action.

However, extraction with water is most advantageous because it is simpler, cheaper and safer in operation.

The residue of the plant tissue is then removed from the extracted solution in conventional manner, for example, by filtration, pressing, centrifugation and the like. After this, undesired impurities such as pigments, low molecular weight substances are removed from the resultant supernatant in order to allow recovery of the active substance of this invention. Preferred methods for this purpose are exemplified as follows.

(A) The supernatant is fractionated by ultrafiltration e.g. using a suitable membrane for retatining substances having a molecular weight of more than 100,000 because the active substance of this invention is present in fractions having a molecular weight of about 100,000 to about 3,000,000 (mainly about 200,000 to about 1,000,000). The ultrafiltration may be effected under suitable pressure, for example, 0.1 to 5 kg/cm$^2$ by using a membrane for retaining substances (B) The supernatant is concentrated, if desired, under reduced pressure and is treated with a hydrophilic organic solvents e.g. ethanol, methanol, propanol, n-butanol, acetone and the like at a convenient concentration e.g. 40–70 w/v % so as to form a precipitate containing the active substance, which is then freeze-dried to obtain a brown powder.

(C) Instead of the organic solvents, it is also possible to add to the supernatant an ammonium salt e.g. ammonium chloride, ammonium sulfate, cetylmethylammonium bromide and the like or an inorganic metalic salt e.g. zinc chloride, copper chloride and the like (e.g. 20–50 w/v %) so as to form a precipitate. The precipitate is desalted and freeze-dried to obtain a brown crude powder.

It is possible to recover the major portion of the active substance present in the starting material (in some cases, more than 90%). However, the quanitity of impurities contained in the crude powder is lowest in the case of (A), and also method (A) may be effected simply and cheaply. Moreover, it has been confirmed that any significant side effect may be avoided even when a large amount of the crude powder obtained by (A) is orally administered to humans and animals and thus this crude powder may be administered orally without further purification.

If desired, the crude powder thus-obtained may further be purified, for example, by column chromatography using a suitable agent for gel filtration or an ion exchanger. In the former case, the elution may be effected with water and in the latter cae, the elution may be effected with a suitable buffer solution. Preferred agents for gel filtration are exemplified by Sephadex G-50 to G-200, Sepharose 2B to 6B, Sephacryl S-200 or S-300 (commercial products of Pharmacia Fine Chemicals AB., Sweden), Bio Gel P-30 to P-300, Bio Gel A (commercial products of Bio-Rad Laboratories Ltd., U.S.A.), Savavac (commercial product of Seravac Laboratories Ltd., U.K.) and the like, and preferred agents for ion exchange treatment are exemplified by QAE-Sephadex A-25 and A-50(Cl$^-$ form), CM-Sephadex C-25 and C-50(Na$^+$ form), SP-Sephadex C-25 and C-50 (Na$^+$ form), DEAE-Sephacel (Cl$^-$ form), DEAE-Sepharose CL-6B (Cl$^-$ form), CM-Sepharose CL-6B (Na$^+$ form) (commercial products of Pharmacia Fine Chemicals AB., Sweden) and the like. It is also possible to use a suitable anion or cation exchange cellulose for the purification. The products thus-obtained may contain certain impurities, although the IF inducing activity is sufficient for practical purposes. If desired, the amounts of impurities may further be reduced by combining these treatments.

According to a further feature of this invention, there is provided a process for inducing IF in the body or cells of animals or humans, comprising administering an effective amount of the IF inducer of this invention to humans or animals. It has been found that by the use of the IF inducer of this invention, any serious toxic trouble which is likely to be inherent to various known IF inducers of microorganism orgin may be avoided. Moreover, when administered to humans, its IF-inducing activity is superior to that of poly I:C or endotoxin and the like. By virtue of this invention, it is thus possible not only to afford high activiral activity to humans and animals, but also to improve their overall healthy conditions. In addition, this active substance is active against certain tumours of animals. It is thus possible to use the IF inducer of this invention not only for preventing and treating various virally cause diseases of various vetebrates such as, e.g. humans, mammals (e.g. cattle, horse, pig etc.), birds (e.g. fowls, duck etc.), fishes (e.g. rainbow trout, yellow tail, eel etc.) and the like but also as anti-tumour agent, agent for improving overall healthy conditions for humans and animals.

The active substance of this invention may be administered e.g. by intravenous or intraperitoneal injection, intestinal or oral administration, spraying and the like.

In the case of the final product of this invention, it may be possible to administer a dose of 0.001 to 100 mg/kg/day by intravenous injection. However, such a dose may vary, depending upon, for example, the type, age and weight of the host and various other conditions, among which the response of the host to IF induction and the purpose of the administration are most important. The active substance of this invention may preferably be administered to animals, for example, at a daily dose of 0.01 to 10 mg/kg (iv.) or 0.1 to 10 mg/kg (ip), and to humans e.g. at a daily dose of 0.01 to 1.0 mg/kg by injection (iv.). In the case of oral administration, it is possible to use, for example, more than about 10 times of the dose for intravenous administration. When the administration is effected topically or in a short period of time, a larger amount of the active substance may be used. When the dose is excessively small, it may be difficult to induce IF in the body or cells of the host. However, the use of an excessively large amount of the active substance of this invention may, in general, give rise to no serious side effect because its toxicity is extremely low.

It has also been found that when a suitable amount of any IF is administered to a host, followed by administration of the IF inducer of this invention, the activity of the IF induced by the active substance of this invention may significantly be enhanced and for example about 3-10 folds activity may be obtained in this manner. Moreover, it is possible to enhance considerably the response of the host to IF induction and also to extend the effective period of time of the IF induced by the IF inducer of this invention.

In the following tests, the used samples were as follows:

Sample A . . . The crude product obtained by the method of Example 1 was freeze-dried.

Sample B . . . The finally purified product of Example 1.

Sample C . . . The finally purified product of Example 2.

Sample D . . . The finally purified product by the method of Example 2 except the use of *Artemisia vulgaris* (type species of the genus Artemisia, U.S. origin)

As test animals, rabbits (same type as that used in hereinafter described preparation example 1), mice (weight 25+1 g; ddy-strain; 6 weeks old) and fowls (weight about 230 g; White Leg Horn) were used.

(A) IF induction and determination of IF activity:
(I) In vitro method:

A spleen cell suspension ($10^7$ cells/ml) was prepared by the method of hereinafter described Experiment 1 using an Eagle MEM medium (commercial product of Nissui Seiyaku K.K., Tokyo) containing a 10% calf serum (which was replaced by a 10% fetal cattle serum in the cases of human tests), each of which fraction (1 ml) was added with the sample of the active substance at a given concentration and incubated at a given temperature. The cultured liquor was centrifuged to separate a supernatant for use to determine the IF activity. Furthermore, in the cases of human tests, the fresh spleen was collected from a man (adult killed by external wounds) and used for the preparation of a leucocytes suspension on each occasion, and also blood was collected from the vein at the armpit of a man (adult, healthy) from which the serum was separated to use for the preparation of a serum suspension on each occasion. The IF activities were determined by using the cells shown in Table 5 by the method of hereinafterdescribed Experiment 1 and indicated in Table 6.

TABLE 5

I — Each group consisting of; II — Cultured for 24 hours at °C.; III — Cells used for determination

|  | I | II | III |
|---|---|---|---|
| Rabbit | 3 | 25 | RK-13 |
| Mouse | 30 | 37 | L |
| Human spleen | 2 | 25 | FL |
| Human leucocytes | 5 | 37 | FL |
| Fowl (White Leg Horn) | 5 | 37 | Fibroblast |

TABLE 6

| | | Concentration of sample (μg/ml) | | | | | |
|---|---|---|---|---|---|---|---|
| | | 100 | 10 | 1.0 | 0.1 | 0.01 | 1.0** |
| Rabbit | A | 200 | 180 | 87 | <5 | <5 | |
| | B | 220 | 205 | 185 | 88 | 28 | |
| | | | | | | | 220 |
| | C | 210 | 200 | 185 | 78 | 25 | |
| | D | 240 | 190 | 190 | 99 | 35 | |
| Mouse | A | 81 | 63 | 30 | <5 | <5 | |
| | B | 120 | 100 | 58 | 28 | 10 | |
| | | | | | | | 120 |
| | C | 116 | 98 | 50 | 26 | 8 | |
| | D | 140 | 115 | 70 | 42 | 18 | |
| Human spleen | A | 28 | 30 | 10 | <5 | <5 | |
| | B | 26 | 34 | 32 | 8 | <5 | |
| | | | | | | | <5 |
| | C | 25 | 33 | 28 | 7 | <5 | |
| | D | 30 | 40 | 32 | 12 | <5 | |
| Human leucocytes | B | 24 | 16 | 11 | <5 | | |
| Fowl | A | 22 | 10 | <5 | | | |
| | B | 44 | 22 | 10 | <5 | | |
| | C | 40 | 18 | 8 | <5 | | |
| | D | 50 | 30 | 15 | <5 | | |

**Control . . . Poly: IC (1.0 μg/ml)

(II) In vivo method:
(1) Rabbit:
Table 2 shows the IF activities induced in rabbits by the method hereinafter described in Experiment 1.

TABLE 2

| | Used sample: sample B* | | | | |
|---|---|---|---|---|---|
| IF activity | Time of collection of blood after administration of sample | | | | |
| (in vitro) | 0 | 1 | 2 | 4 | 6 (hour) |
| Rabbit 1 | <10 | 55 | 480 | 95 | 44 |
| Rabbit 2 | <10 | 25 | 230 | 50 | 23 |

*Dose: 500 μg/ml

Similar treatments were repeated by changing the dose of the sample stepwise within a range of 4 to 0.004 mg/kg, and it was found that the IF activity induced in the serum reached its maximum 2 hours after administration. Also, the maxium was observed about 10 to 13 hours after oral administration.

(2) Mouse:
Mice (each group consisiting of 10 mice) were used as test animals and treated as follows.

(a) Each 0.1 ml of a physiological solution of sodium chloride containing a given amount of sample B shown in Table 4 was injected into the vein at the tail of each mouse which was then allowed to stand for 1, 2, 3 or 5 hours, or (b) Each 0.2 ml of a physiological solution of sodium chloride containing a given amount of sample B shown in Table 4 was administered (ip.) to each mouse which was then allowed to stand for 2, 4 or 6 hours, or (c) Water (0.2 ml) containing a given amount of sample B shown in Table 4 was orally administered to each mouse which was then allowed to stand for 2.5, 5, 7.5 or 10 hours.

On each occasion, the test animal was then sacrificed by cardic puncture. Blood was collected from each mouse and used to prepare the serum. The IF activity induced was determined in a similar manner to that described above. It was observed that the IF activity reached its maximum about 2 hours in the case (a), about 3-4 hours in the case (b) and about 7.5-10 hours in the case (c), after administration. Table 7 indicates the maximum IF activities (means value). A similar tendency was also found when the same treatments were repeated by using sample A instead of sample B.

TABLE 7

| Maximum IF activity in vivo (mouse) | | | |
|---|---|---|---|
| Concentration (mg/kg) | Iv. | Ip. | Oral |
| 4000 | | | 18 |
| 400 | | | 14 |
| 40 | 510 | 76 | 10 |
| 4 | 176 | 36 | <5 |
| 0.4 | 108 | 20 | |
| 0.04 | 45 | <5 | |
| 0.004 | 15 | <5 | |
| Untreated | <5 | <5 | <5 |

(3) Humans:

Each 200 mg of sample B was orally administered to each of five men (adults, healthy). Blood was collected from the vein at the arm of such volunteer after 13 hours from administration and used for the preparation of the serum which was then treated in a similar manner to that described above to determine the IF activity of about 14 units (mean value).

(4) Fowl:

Fowls (each group consisting of 10 fowls) were used as test animals. A physiological solution of sodium chloride (each 0.2 ml) containing sample B (4 mg/kg) was administered into the vein under the wing of each animal. After 2 hours on each occasion, the fowl was sacrificed by cardic puncture. Similarly, blood was collected for use to determine that the IF activity induced in the serum was about 26 units.

(B) Protection against viral infections:

(1) Mouse: (Vaccinia virus)

Mice (each group consisting of 20 female) were used as test animals, to each of which was administered a physiological solution of sodium chloride (each 0.2 ml) containing a given amount of the sample shown in Table 5 by injection (ip. or iv.) or orally. After 24 hours, each mouse was infected with Vaccinia virus [30 PFD contained in 0.1 ml of a physiological sodium chloride solution] [1 PFD denotes an amount of the virus capable of forming the pocks at the tails of 50% of the mice used] by injection into the vein at the tail. For 9 days after this, the numbers of the pocks formed at the tail were compared with the corresponding numbers of the pocks found in the untreated mice to determine the inhibition ratio. A ratio of 50% was evaluated as an effective ratio. The numbers of pocks of untreated mice were 29.5 in average. The results are shown in Table 8.

TABLE 8

| Method of administration | Concentration (mg/kg) | Inhibition ratio % (average) Sample | | | |
|---|---|---|---|---|---|
| | | A | B | C | D |
| Iv. | 40 | 93 | 100 | 100 | 100 |
| | 4 | 71 | 90 | 89 | 92 |
| | 0.4 | 69 | 69 | 70 | 80 |
| | 0.04 | 55 | 65 | 62 | 65 |
| | 0.004 | 20 | 45 | 38 | 50 |
| Ip. | 40 | 73 | 78 | 75 | 92 |
| | 4 | 71 | 72 | 70 | 85 |
| | 0.4 | 40 | 68 | 66 | 74 |
| | 0.04 | 20 | 38 | 37 | 56 |
| | 0.004 | 11 | 22 | 20 | 27 |
| Oral | 4000 | 42 | 53 | 51 | 60 |
| | 2000 | 38 | 50 | 48 | 55 |
| | 400 | 10 | 22 | 20 | 35 |

(2) Mouse: (Herpes Simplex virus):

Similar treatments to those described above (B,1) were repeated, but Vaccinia virus was replaced by Herpes Simplex virus which was infected to each test animal by injection (iv. or ip.). The results were observed for 30 days to determine the average survival days which were then compared with the corresponding days of untreated group. A significant survival effect was observed.

(3) Rabbit (Vaccinia virus):

(a) Rabbits (each group consisting of 5 rabbits) were used. A physiological sodium chloride solution (0.1 ml) containing a given amount of sample A was injected under the skin at the back of each rabbit, and after 24 hours, 10 $ID_{50}$ of Vaccinia virus [1 $ID_{50}$ denotes an amount of the virus capable of forming at least on pock of more than 6×6 mm in size under the skin of 50% of the test rabbits] was injected into the same place in a similar manner to that used for administration of the sample. After 7 days from the infection, the formed pocks were counted and compared with the corresponding numbers of the pocks of untreated rabbits. The concentration of the sample was changed step by step from 0.02 to 200 μg/kg. It was found that a dose of more than 2 μg/kg gave a 100% inhibition.

(b) Rabbits (each group consisting of 5 rabbits) were used as test animals. Each 100 mg/day of sample A was orally administered to each rabbit on the 1st, 3rd, 4th, 6th and 8th day (500 mg/kg in total). On the 5th day, 10 $ID_{50}$ and 100 $ID_{50}$ of Vaccinia virus were independently administered under the skin at the back of each rabbit. On or before 12th day, no pock was formed at the back of the rabbits infected with 10 $ID_{50}$ and weak pocks were found at the back of the rabbits infected with 100 $ID_{50}$. However, in the latter case, the pocks were completely disappeared 2 weeks after infection.

(C) Anti-tumour effect (mouse):

(1) Ehrlich ascites tumour:

Mice (each group consisting of 15 mice) were used. A sterilized water (0.2 ml) containing Ehrlich ascites tumour ($2.5 \times 10^6$ cells) was injected (ip.) into each of the mice. After 24 hours from this, a given amount of sample B was added to a sterilized water (0.2 ml) and administered to each animal. The administration was effected once daily at a daily dose of 0.2, 1.0 or 5 mg/kg (ip.) or 40, 200 or 1000 mg/kg (orally). The administration was continued for 14 days. As a result of injection (ip.) at a dose of 1 or 5 mg/kg/day, the median survival days of the test animals were 33 days. ⅓ of the mice were still alive on or before the 50th day after transplantation and moreover completely cured. However, control mice were not alive on the 29th day after transplantation.

A similar effect was observed when 5 equal parts (each 1.0 mg/kg) of sample B were injected (ip.) to the mice at an interval of 3 days. The results obtained by continuous administration of sample B (1000 mg/kg, oral) were substantially the same as the results obtained by injection (ip.).

(2) S-180 Sarcoma solid tumour:

A sterilized water (0.2 ml) containing S-180 Sarcoma solid tumour ($1 \times 10^5$ cells) was injected under the skin of the armpit of each of the test mice (each group consisting of 15 mice) and sample B was administered in a similar manner to that described above. By injection (ip.) at a dose of 5 mg/kg/day, the median survival days were 40 days and the tumours of 5 mice were reduced to about ⅓ in size on or before 40 days from transplantation. By oral administration at a dose of 400 or 1000 mf/kg/day the results were not superior to the results obtained by injection (ip.). All untreated mice deceased on or before the 35th day from the transplantation.

(D) Combined use of IF and IF inducer (Priming effect):

(1) A suspension containing lymphoid cells of rabbit ($10^7$ cells/ml) was prepared by the method of hereinafter described Experiment 1 and was added with rabbit IF (30 unit/ml). The mixture was treated at 37° C. for 6 hours and was then centrifuged to remove the IF. After this, an Eagle MEM medium (1 ml) and sample B were added to the cells and its activity was determined with simultaneous change of the amount of sample B from $10^{-3}$ to $10^{-7}$ mg/ml. It was found that the activity of the induced IF raised to about 3–10 folds and also the response of the cells was significantly improved.

(2) By the method of hereinbefore described (D,1), a suspension of human spleen cells ($10^7$/ml) was prepared and treated with human IF (100 unit). The activity of the IF induced raised to about 3–10 folds and also the response of the cells to IF induction was significantly improved.

(3) Rabbits (each group consisting 5 rabbits) were intravenously administered with rabbit IF ($10^6$ unit). 6 hours after this, sample B was administered in a similar manner to that described in (A,II,1). It was observed that the IF activity induced in the serum raised to about 3–6 folds and the period of time of response to the IF inducer was also extended.

(4) Each of 5 rabbits were injected (ip.) with rabbit IF ($10^6$ unit) and 24 hours after this an infection test was effected in a similar manner to that described in (B, 3, b). No pock was formed at the back of the test animal by infection of the virus at a dose of 100 $ID_{50}$, and weak pocks were formed at the back of about ⅓ of the test animals infected with 100 $ID_{50}$ of the virus. However, in the latter case, the pocks completely disappeared within 2 weeks after infection.

(E) Toxicity:

(1) Acute toxicity;

A physiological solution of sodium chloride containing a given amount of sample B was administered to each of the test animals [groups of mice, each consisting of 20 mice; male and female, and groups of rats, each consisting of 20 rats, weight 95 g; SPF; 6 weeks old, male and female] to give the $LD_{50}$ values shown in Table 10. No significant difference was observed between male and female.

TABLE 9

| Animal | Acute toxicity ($LD_{50}$; g/kg) | | | |
|---|---|---|---|---|
|  | Subcutaneous | Ip. | Iv. | Oral |
| Mouse | >2 | >1 | 0.90 | >5 |
| Rat | >1 | >1 | 0.95 | >5 |

(2) Subacute toxicity:

(a) Rats (weight about 95 g; SPF-SD strain; 6 weeks old; each group consisting of 20 rats) were used as test animals. Sample A was divided into fractions (0.35, 0.7, 1.4 and 2.8 g/kg), each of which was added to each sterilized water (from 0.25 to 0.5 ml), and a given amount of the sample was daily administered to the test animals compulsively by using a canule. The administration was continued for 3 months. In comparison with the untreated animals, the healthy conditions of the test animals were improved throughout the test period and their body weights increased at a remarkably high ratio. All animals were dissected after the end of 3 months and investigated pathologically. However, it was difficult to determine the subacute toxicity reasonably because no significant change was observed pathologically.

(b) Five healthy men (adults) were administered orally with sample A (200 mg/day) and the administration was continued for 10 days. As a result, no significant side effect was observed and also overall healthy conditions were improved. The dose of this was comfortable and refreshed them in mind and body.

From these results, it is apparent that the IF inducer of this invention is extremely low toxic and thus even when administered over extended period of time, no significant side effect may be observed in practice.

For the purpose of administering the active substance of this invention to humans and animals, there is provided a pharmaceutical composition, comprising as active ingredient the active substance of this invention in association with a pharmaceutical carrier or excipient. The composition may be in any and all forms adapted to oral, rectal, parenteral, percuteneous, intramucous administration and the like. Thus, for example, the composition may be solid or liquid for oral administration and may take the form of powders, syrups, capsules, granules, emulsions, suspensions, drops and the like. Such composition comprises carrier or excipient conventionally used in the pharmaceutical art. Thus, for example, suitable tabletting excipients include lactose, potato and soluble starches and magnesium stearate and for parenteral administration, the carrier may be a sterile water, physiological solution of sodium chloride, armond oil and the like, which may be put in an ampule or may be added to the active substance before use.

The composition may, if desired, further comprise, for example, bonding agents, stabilizing agents, emulsifiers, suspending agents, dispersing agents, lubricants, antiseptic agents, fillers and the like conventionally used in the pharmaceutical art.

For practical purpose, the composition may be formulated, for example, as buccals, troches, eye drops, suppositories and the like for intramucous administration, solutions, oils, suspensions and the like for injection agents, inhalants, sprays and the like for inhalational administration and ointments, plasters, liniments, bathes, sprays and the like for external administration.

Advantageously, the composition may be formulated as dosage units, each unit being adapted to supply a fixed dose of active ingredient. Suitable dosage unit forms are, for example, tablets, coated tablets, ampules, capsules, suppositories and the like.

The amount of the active ingredient preferably contained in such dosage unit forms may, for example, be within a range of from 4 to about 10 for oral administration, about 2-3 for subcutaneous administration, about 1.5-3 for intramuscular administration, about 2-4 for baccals and troches and about 5-10 for suppositories, calculated on the basis of the preferred amount for intravenous injection.

The compositions are exemplified as follows.

| (1) Parenteral injection: | | |
|---|---|---|
| Physiological solution of NaCl | 1.0 | ml |
| Sample B | 0.01 | g |
| packed and sealed in a 2 ml ampule under sterilized conditions. | | |
| (2) Troch: | | |
| White sugar | 1 | g |
| Sample B | 0.05 | g |
| Starch | 0.05 | g |
| (3) Suppository: | | |
| Polyethylene glycol 400 | 0.8 | g |
| Liquid polyethylene glycol 1500 | 0.2 | g |
| Sample A | 0.2 | g |
| (4) Syrup: | | |
| CMC—Na | 0.2 | g |
| Simple syrup | 20 | g |
| Ethylparaffin | 0.04 | g |
| Sample B | 0.1 | g |
| (5) Ointment: | | |
| Purified lanolin | 5 | g |
| Yellow wax | 5 | g |
| White vaselin | 87 | g |
| Sample B | 3 | g |
| (6) Liniment: | | |
| Potassium hydroxide | 0.3 | g |
| Glycerin | 20 | ml |
| Ethanol | 25 | ml |
| Sample B | 2.5 | g |
| Water | | |
| Total | 100 | ml |

DRAWINGS

FIGS. 1 and 2 show respectively the ultraviolet and infrared absorption spectra of the active substance of this invention.

The following non-limiting examples illustrate the preparation of the active substance of this invention.

EXAMPLE 1

In the first step, dried leaves (1 kg) of *Artemisia princeps* Pamp. were washed with water and allowed to stand in water (20 l) at room temperature for 3 days to effect extractions, followed by centrifugation (6000 r.p.m.) for 20 minutes to remove the residue which was washed twice with water (each 5 l). The washing liquid was combined with the extracted suernatant. The solid content in the combined solutions was 138.735 g (dry basis). The combined solutions were fractionated by ultrafiltration using an ultrafilter (Model UD-6, commercial product of Bio Engineering K.K., Tokyo) with an UK-200 membrane (commercial product of Toyo Roshi K.K., Tokyo) for retaining substance having a molecular weight of more than 200,000 at a pressure of 3 kg/cm³ to give a residue which was then freeze-dried to obtain a brown powder (19.676 g). For comparison, a similar treatment to that described above was effected by using a membrane (XM 100 A) for retaining substances having a molecular weight of more than 100,000 to give a brown powder (20.835 g).

In the second step (purification), the first crude powder (1.5 g) was dissolved in water (5 ml) and transferred to a column (4.5×70 cm) packed with Sephdex G-200 (an agent for gel filtration). The elution was effected with water (600 ml) and the effluent was divided into fractions (each 3 ml). Fraction Nos. 27 to 60 were collected and combined and the combined fractions were freeze-dried to obtain a whitish powder (220 mg).

In the third step (further purification), this powder (100 mg) was dissolved in a 0.1 M tris-HCl buffer solution (5 ml; pH 7.0; I=0.01) and transferred to a column (2.5×70 cm) packed with DEAE-Sephadex A-50 (ion exchanger). A 0.1 M tris-HCl buffer solution (300 ml; pH 9.0; containing 0.5 M NaCl) was used for elution and the effluent was divided into fractions (each 3 ml). Fraction Nos. 15 to 30 were collected and combined and the combined fractions were freeze-dried to obtain a whitish amorphous powder (62.7 mg) containing smaller amounts of impurities and having substantially the same IF inducing activity when compared with the first whitish powder. The final product had the physicochemical characteristics as hereinbefore defined and its high purity was confirmed by ultracentrifugation and electrophoresis.

For comparison purpose, the IF inducing activities of the substances obtained by respective steps in this example were determined in a similar manner to that hereinafter described in Experiment 1 (in vitro method) to give the following results.

TABLE 10

| Step | Sample (after) | Activity at a concentration of sample ($\mu$g/ml) | | |
|---|---|---|---|---|
| | | 10 | 1.0 | 0.1 |
| 1 | Extraction | >100 | <10 | <10 |
| 1 | Ultrafiltration | >100 | 88 | <10 |
| 2 | Gel filtration | >100 | >100 | 93 |
| 3 | Ion exchange treatment (final product) | >100 | >100 | >100 |

EXAMPLE 2

A similar treatment to that described in Example 1 was carried out with the exception that *Artemisia capillaris* Thun. was extracted by allowing the leaves to stand in water at room temperature for 2 hours, adding to the water 1 N sodium hydroxide to adjust the pH to 8.5, followed by further extraction at 65° c. for 2 hours. The physicochemical characteristics of the final product (60.2 mg) were substantially the same as those of the final product obtained by Example 1.

EXAMPLES 3-26

The leaves, stems and seeds of the dried plants as shown in the following Table 6 were independently treated in a similar manner to that described in Example 1. The products obtained by the second step of all examples were independently treated in a similar manner to that hereinafter described in Experiment 1 (in vitro method) to determine their IF inducing activities. The results are shown in the following Table 6. The physicochemical characteristics of the final products obtained by Examples 3-26 were substantially the same as those of the final product of Example 1.

TABLE 6

A: Seed, B: Stem, C: Leaf

| No. | Artemisia | Tissue | IF activity at (concentration of sample) 10 | 1.0 | 0.1 μg/ml |
|---|---|---|---|---|---|
| 1 | A. princeps Pamp. | A | >100 | >100 | 80 |
|  |  | B | >100 | >100 | 94 |
|  |  | C | >100 | >100 | 93 |
| 2 | A. capillaris Thun. | A | >100 | >100 | 80 |
|  |  | B | >100 | >100 | 90 |
|  |  | C | >100 | >100 | 85 |
| 3 | A. absinthium L. | A | >100 | >100 | 60 |
|  |  | B | >100 | >100 | 90 |
|  |  | C | >100 | >100 | 92 |
| 4 | A. maritima L. | A | >100 | >100 | 55 |
|  |  | B | >100 | >100 | 80 |
|  |  | C | >100 | >100 | 85 |
| 5 | A. kurramensis Qaz. | A | >100 | >100 | 80 |
|  |  | B | >100 | >100 | 85 |
|  |  | C | >100 | >100 | 80 |
| 6 | A. montana Pamp. | A | >100 | >100 | 90 |
|  |  | B | >100 | >100 | 95 |
|  |  | C | >100 | >100 | 95 |
| 7 | A. feddei Lev. et Van. | A | >100 | >100 | 70 |
|  |  | B | >100 | >100 | 75 |
|  |  | C | >100 | >100 | 70 |
| 8 | A. japonica Thun. | A | >100 | >100 | 90 |
|  |  | B | >100 | >100 | 95 |
|  |  | C | >100 | >100 | 94 |
| 9 | A. keiskeana Miq. | A | >100 | >100 | 90 |
|  |  | B | >100 | >100 | 90 |
|  |  | C | >100 | >100 | 85 |
| 10 | A. stolonifera Komar. | A | >100 | >100 | 60 |
|  |  | B | >100 | >100 | 75 |
|  |  | C | >100 | >100 | 70 |
| 11 | A. monophylla Kitam. | A | >100 | >100 | 55 |
|  |  | B | >100 | >100 | 70 |
|  |  | C | >100 | >100 | 70 |
| 12 | A. stelleriana Bess. | A | >100 | >100 | 90 |
|  |  | B | >100 | >100 | 85 |
|  |  | C | >100 | >100 | 90 |
| 13 | A. vulgaris L. | A | >100 | >100 | 95 |
|  |  | B | >100 | >100 | 98 |
|  |  | C | >100 | >100 | 99 |
| 14 | A. abrotanum L. | A | >100 | >100 | 90 |
|  |  | B | >100 | >100 | 93 |
|  |  | C | >100 | >100 | 95 |
| 15 | A. campestris L. | A | >100 | >100 | 70 |
|  |  | B | >100 | >100 | 93 |
|  |  | C | >100 | >100 | 95 |
| 16 | A. vallesiaca All. | A |  |  |  |
|  |  | B | >100 | >100 | 92 |
|  |  | C | >100 | >100 | 99 |
| 17 | A. molinieri Quez. | A |  |  |  |
|  |  | B | >100 | >100 | 95 |
|  |  | C | >100 | >100 | 96 |
| 18 | A. dracunculus L. | A |  |  |  |
|  |  | B | >100 | >100 | 97 |
|  |  | C | >100 | >100 | 95 |
| 19 | A. ludoviciana Nutt. | A |  |  |  |
|  |  | B | >100 | >100 | 92 |
|  |  | C | >100 | >100 | 95 |
| 20 | A. arbuscula Nutt. | A |  |  |  |
|  |  | B | >100 | >100 | 89 |
|  |  | C | >100 | >100 | 96 |
| 21 | A. tridentata Nutt. | A | >100 | >100 | 90 |
|  |  | B | >100 | >100 | 93 |
|  |  | C | >100 | >100 | 95 |
| 22 | A. filifolia Torr. | A |  |  |  |
|  |  | B | >100 | >100 | 88 |
|  |  | C | >100 | >100 | 94 |
| 23 | A. caudata Michx. | A |  |  |  |
|  |  | B | >100 | >100 | 93 |
|  |  | C | >100 | >100 | 95 |
| 24 | A. lindleyana Bess. | A |  |  |  |
|  |  | B | >100 | >100 | 96 |
|  |  | C | >100 | >100 | 97 |
| 25 | A. frigida Willd. | A |  |  |  |
|  |  | B | >100 | >100 | 98 |
|  |  | C | >100 | >100 | 95 |
| 26 | A. biennis Willd. | A |  |  |  |
|  |  | B | >100 | >100 | 89 |
|  |  | C | >100 | >100 | 90 |

EXPERIMENT 1

Determination of IF induced by IF inducer and IF assay: [Reference: Y. Kojima's report in Kitasato Arch. Med., 43:35 (1970)]

(a) IF induction in vitro:

A rabbit (weight about 1 kg; New Zealand White; SPF) was sacrificed by cardic puncture and its spleen, bone marrow and lymph node cells were collected and combined together, from which a cell suspension containing the mixed cells ($10^7$ cells/ml) was prepared using an Eagle MEM medium (commercial product of Nissui Seiyaku K.K., Tokyo) containing a 10% calf serum. This suspension was divided into fractions (each 1 ml), and 4 fractions were respectively added with 10, 1.0, 0.1 and 0.01 μg/l of an active substance prepared by the method of Example 1, which was incubated at 25° C. for 24 hours, followed by centrifugation to obtain each supernatant which was then used to determine the activity of the IF induced.

(b) IF induction in vivo:

An aqueous solution (2 ml) of the active substance prepared by the method of Example 1 (500 μg/ml) was injected into the auticular vein of a rabbit (weight about 1 kg; New Zealand White; SPF). 1, 2 4 and 6 hours after this, a 2 ml sample of blood was removed from the rabbit on each occasion and used to prepare the serum used to determine the IF activity.

(c) Determination of IF activity:

In both (a) and (b), the activity of the IF induced was determined in reliance with the reduction ratio of plaques in the following manner.

A monolayer culture of the lined cells RK-13 of rabbit was put in a dish and added with a predetermined amount of the solution obtained by the method (a) or (b) (suitably diluted). The culture was incubated at 37° C. overnight with addition of Vesicular stomatitis virus used as the challenge virus. The IF activity is indicated by the reduction ratio of plaques and the unit of the IF activity is expressed by the reciprocal number of the highest dilution of the sample required for reducing the numbers of plaques to 50%.

EXPERIMENT 2

Definition of IF inducer:

The active substance of this invention represents an IF inducer because the samples prepared by the methods (a) and (b) are capable of inhibiting the growth of Vesicular stomatitis virus and Vaccinia virus in the lined RK-13 cells of rabbits of the same animal species, but do not inhibit the growth of Vesicular stomatitis virus in L cells of mice i.e. of a different animal species, and moreover, their IF activities are inactivated by treating with 0.08% trypsin at 37° C. for 2 hours. It has also been found that the IF induced by the active substance of this invention is stable when dialized against a pH 2 buffer solution at 5° C. for 2 days, unstable on heating at 60° C. for 2 hours, gives no precipitate by centrifugation at 100,000 xg for 2 hours and is non-toxic against the cells at the minimum virus-inhibitory level.

The IF induced by the active substance of this invention may be classified into Type-I IF and consists of a complex of α- and β-types. Also it has been observed that IF is induced when the active substance of this invention is used, for example, for treating the cells of bone marrow, lymph node, spleen and the like in vitro or injected into the body of animals, but no IF is induced when applied to treat the primary or continuous cell cultures which are known to induce IF by viral infection or treating with poly I:poly C.

EXPERIMENT 3

In Example 1, the electrophoresis was effected at 4° C. in conventional manner using a commercially available device (Model AE-2, product of Toyo Kagaku Sangyo K.K., Tokyo), a polyacrylamide gel plate (thickness 3 mm) and a 0.3M boric acid buffer (pH 8.4). The resultant single band indicated that the rest sample had a high putity.

EXPERIMENT 4

Determination of the specific IF activity in vitro:

(A) In a similar manner to that described in Example 1, dried leaves (1 kg) of *Artemisia princeps* Pamp. were extracted with water (20 l) to give an extracted solution (dry weight 138.735 g) which was subjected to ultrafiltration using a membrane (UK-200) capable of fractionating substances having a molecular weight of more than 200,000 to give a residue and filtrate. The residue was freeze-dried to obtain a crude powder (dry weight 19.676 g) referred to as Fraction No. I. The filtrate was similarly treated with a membrane (UK-10, commercial product of Toyo Roshi K.K., Tokyo) capable of fractionating substances having a molecular weight of more than 10,000 to give a residue and filtrate, which were freeze-dried respectively to give solid substances referred to as Fraction II (dry weight 4.415 g) and Fraction III (dry weight 114.644 g). IF activities induced in vitro by these fractions were determined by the method of Experiment 1 to discover that Fraction I was active and no or little activity was present in Fractions II and III. Subsequently, Fraction I (1.5 g) was dissolved in water (5 ml) and applied to a column (4.5×70 cm) packed with Sephadex G-200 (commercial product of Pharmacia Fine Chemicals AB., Sweden). Gel filtration was effected with water (600 ml) and the effluent was divided into fractions (each 3 ml). Each fraction was used to determine the absorbance at 400 mμ with a spectrometer (Model 40-100, commercial product of Hitachi Limited, Tokyo). In reliance with the resultant peaks, these fractions were classified and combined into 5 groups. Each group was freeze-dried and used to determine the IF activity induced in vitro by the method of Experiment 1. The results are shown in the following table.

TABLE A

| Fraction (molecular weight) | Yield (%)* | Recovery ratio (%) | IF activity in vitro at a concentration of | | |
|---|---|---|---|---|---|
| | | | 10 | 1.0 | 0.1 μg/ml |
| After ultrafiltration | | | | | |
| All extracts | 13.87 | | >100 | <10 | <10 |
| I (>200,000) | 1.97 | 14.20 | >100 | 88 | <10 |
| II (200,000–10,000) | 0.44 | 3.17 | 56 | <10 | <10 |
| III (<10,000) | 11.46 | 82.63 | <10 | <10 | <10 |
| After gel filtration | | | | | |
| I-1** | 0.21 | 10.61 | >100 | >100 | 93 |
| I-2 | 0.11 | 5.55 | 70 | <10 | <10 |

TABLE A-continued

| Fraction (molecular weight) | Yield (%)* | Recovery ratio (%) | IF activity in vitro at a concentration of | | |
|---|---|---|---|---|---|
| | | | 10 | 1.0 | 0.1 μg/ml |
| I-3 | 0.14 | 7.07 | <10 | <10 | <10 |
| I-4 | 1.46 | 73.74 | <10 | <10 | <10 |
| I-5 | 0.06 | 3.03 | <10 | <10 | <10 |

*100% = dry weight of starting material
**Fraction Nos. 27–60 in Example 1

(B) In a similar manner to that described in Example 1, dried leaves of *Artemisia princeps* Pamp. (10 g) were extracted with water (200 ml) at room temperature for two hours, heated at 65° C. for one hour, adjusted to pH 8.5 with addition of 1 N NaOH solution, heated at 65° C. for 2 hours, cooled to room temperature and centrifuged for 30 minutes (7000 r.p.m.) to remove the residue from the supernatant. The residue was washed twice with water (each 40 ml) and the washing liquid was combined with the supernatant. The combined solutions (dry weight 1.5 g) were subjected to ultrafiltration using a membrane (UK-200) capable of fractionating substances having a molecular weight of more than 200,000 in a similar manner to that described in Example 1 to give a filtrate and residue. The residue was freeze-dried to obtain a crude powder (dry weight 0.11 g) referred to as Fraction No. I. The filtrate was treated similarly by using a membrane (UK-10, commercial product of Toyo Roshi K.K., Tokyo) capable of fractionating substances having a molecular weight of more than 10,000 to give a residue and filtrate, both of which were freeze-dried to obtain solid substances referred to as Fractions II (dry weight 0.091 g) and III (dry weight 1.277 g) respectively. Fraction No. 1 was subjected to gel filtration and freeze-dried in a similar manner to that described in Example 1. All resultant substances were used to determine the IF activities induced in vitro by the method of Experiment 1. The results are shown in Table B.

TABLE B

| Fraction (molecular weight) | Yield (%)* | Recovery ratio (%) | IF activity in vitro at a concentration of | | |
|---|---|---|---|---|---|
| | | | 10 | 1.0 | 0.1 μg/ml |
| All extracts | 15.00 | | 90 | <10 | <10 |
| I (>200,000) | 1.09 | 7.38 | >100 | 94 | <10 |
| II (200,000–10,000) | 0.91 | 6.16 | 53 | <10 | <10 |
| III (10,000) | 12.77 | 86.46 | <10 | <10 | <10 |

*100% = dry weight of starting material (C) From (A) and (B), it is apparent that the IF-inducing activity is most prevalent in the fraction having a molecular weight of more than 200,000 and that impurities contained in the extracted solution were almost completely removed by ultrafiltration and gel filtration (more than 98%). The amounts of the impurities were further reduced by the following ion exchange treatment, as described in Example 1, and an increase of about 10% of the specific activity was observed.

We claim:

1. A process for producing a water-soluble interferon inducer from a plant tissue, comprising extracting said interferon inducer with water from the tissue of a plant belonging to the genus Artemisia containing said interferon inducer at a temperature of from ambient to the boiling point of the extraction mixture for a period of up to 5 days sufficient to extract the major portion of said interferon inducer present in said tissue, forming a supernatant from the extracted solution, fractionating the supernatant to yield fractions containing the major portion of said interferon inducer present in the supernatant, and recovering said interferon inducer therefrom.

2. The process of claim 1, wherein the plant is selected from

*Artemisia princeps* Pamp; *A. absinthium* L.; *A. maritima* L.; *a. kurramensis* Qaz.; *A. montana* Pamp.; *A. feddei* Lev. et Van.; *A. japonica* Thun.; *A. keisumeana* Miq.; *A. stolonifera* Komar.; *A. monophylla* Kitam.; *A. stelleriana* Bess.; *A. capillaris* Thun.; *A. vulgaris* L.; *A. abrotantum* L.; *A. vallesiaca* All.; *A. dracunculus* L.; *A. ludoviciana* Nutt.; *A. arbuscula* Nutt.; *A. tridentata* Nutt.; *A. filifolia* Torr.; *A. caudata* Michx.; *A. lindleyana* Bess.; *A. frigida* Willd.; *A. biennis* Willd.; *A. campestris* L.; *A. molinieri* Quez and variants thereof.

3. The process of claim 1 wherein the extracting water has a pH of from 7 to 10.

4. The process of claim 3, wherein the pH is 7–10.

5. The process of claim 1, wherein the supernatant is fractionated by ultrafiltration.

6. The process of claim 5, wherein the ultrafiltration is effected by using an ultrafiltration membrane for retaining substances having a molecular weight of more than 100,000.

7. The process of claim 1, wherein the fractionation is effected by adding to the supernatant one member selected from hydrophilic organic solvents incapable of dissolving the said interferon inducer and ammonium salts so as to form a precipitate containing a major portion of the said interferon inducer.

8. The process of claim 7, wherein the organic solvent is selected from methanol, ethanol, propanol, butanol, acetone and mixture thereof at a concentration of 40–70 w/v %.

9. The process of claim 7, wherein the ammonium salt is selected from ammonium chloride, ammonium sulfate and cetylmetylammonium bromide at a concentration of 20–50 w/v %.

10. An amorphous whitish powder effective as an interferon inducer made by the process of claim 1.

11. A pharmacutical composition in dosage unit form, comprising as active ingredient an interferon inducer claimed in claim 10 in association with a pharmacutical carrier or excipient, said dosage unit containing from about 0.001 mg to 13 g of the said active ingredient.

12. The interferon inducer of claim 10 having a molecular weight of about 100,000 to about 3,000,000.

13. A pharmaceutical composition comprising as an active ingredient an interferon inducer made by the process of claim 1 in association with a pharmaceutical carrier or excipient.

14. The pharmaceutical composition of claim 13 wherein said interferon inducer has a molecular weight of about 100,000 to about 3,000,000.

15. The process of claim 1 wherein said interferon inducer has a molecular weight of about 100,000 to about 3,000,000.

* * * * *